(12) United States Patent
Haddad et al.

(10) Patent No.: US 9,517,468 B2
(45) Date of Patent: Dec. 13, 2016

(54) METHODS AND SYSTEMS FOR CALIBRATION OF A POSITIONAL ORIENTATION BETWEEN A SAMPLE CONTAINER AND NOZZLE TIP

(75) Inventors: Antoine E. Haddad, Newark, DE (US); John Esposito, Williamstown, NJ (US); Joseph Brennan, Newark, DE (US); John Mizzer, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 464 days.

(21) Appl. No.: 14/005,017

(22) PCT Filed: Mar. 16, 2012

(86) PCT No.: PCT/US2012/029488
§ 371 (c)(1),
(2), (4) Date: Sep. 13, 2013

(87) PCT Pub. No.: WO2012/129105
PCT Pub. Date: Sep. 27, 2012

(65) Prior Publication Data
US 2013/0345894 A1   Dec. 26, 2013

Related U.S. Application Data

(60) Provisional application No. 61/454,293, filed on Mar. 18, 2011.

(51) Int. Cl.
*B01L 3/00*   (2006.01)
*G01N 35/10*  (2006.01)

(52) U.S. Cl.
CPC ............ *B01L 3/56* (2013.01); *G01N 35/1011* (2013.01)

(58) Field of Classification Search
CPC  B01L 3/56; G01N 35/1011; G01N 2035/1016
See application file for complete search history.

(56) References Cited

U.S. PATENT DOCUMENTS 4,311,959 A * 1/1982 Riessland ............... G01B 7/08
324/662
4,318,483 A   3/1982 Lombardo et al.
(Continued)

FOREIGN PATENT DOCUMENTS

WO   2009039122 A2   3/2009

OTHER PUBLICATIONS

PCT International Search Report and Written Opinion dated Jul. 13, 2012 (8 Pages).

*Primary Examiner* — Kenneth M Lo
*Assistant Examiner* — David Wynne (57) ABSTRACT

Disclosed are methods to aid in a calibration of a vertical orientation of a nozzle tip to a sample container in a processing or testing system. The method includes positioning the nozzle over a calibration target at a home height location (HM), moving the nozzle downward a distance (D) until contact with the calibration target is sensed, positioning the nozzle over the sample rack and moving the nozzle downward until contact with a registration location is sensed, imaging the sample rack and calibration target to determine a height (H) between the registration location and calibration target, and calculating a translation ratio (TR) between the height (H) measured in pixel space and the distance (D) measured in machine space. The translation ratio (TR) may be used to drive the nozzle tip to a predetermined depth. A robot calibration system is disclosed, as are other aspects.

10 Claims, 10 Drawing Sheets (56) References Cited

U.S. PATENT DOCUMENTS

| | | | |
|---|---|---|---|
| 5,141,871 A * | 8/1992 | Kureshy | G01N 35/1083 356/621 |
| 5,148,963 A * | 9/1992 | Hicks | B23K 3/06 228/102 |
| 5,297,238 A * | 3/1994 | Wang | B25J 9/1692 700/254 |
| 6,080,364 A | 6/2000 | Mimura et al. | |
| 6,426,225 B1 | 7/2002 | Lewis et al. | |
| 6,516,244 B1 * | 2/2003 | Yoo | H01L 21/681 414/936 |
| 6,798,925 B1 * | 9/2004 | Wagman | G06T 7/0018 356/620 |
| 7,040,137 B1 * | 5/2006 | Gieskes | H05K 13/0452 250/252.1 |
| 7,112,812 B2 * | 9/2006 | Schauer | G01B 11/005 250/559.29 |
| 7,581,331 B2 | 9/2009 | Wong et al. | |
| 8,135,208 B1 * | 3/2012 | Vangal-Ramamurthy | G06T 7/0018 348/E17.002 |
| 2002/0108239 A1 * | 8/2002 | Isogai | H05K 13/0413 29/834 |
| 2004/0241872 A1 * | 12/2004 | Wegrzyn | B01J 19/0046 436/171 |
| 2008/0056956 A1 * | 3/2008 | Vijay | B01L 3/5082 422/562 |
| 2008/0261294 A1 | 10/2008 | Noda et al. | |
| 2009/0180931 A1 * | 7/2009 | Silbert | G01N 35/0099 422/63 |
| 2009/0324032 A1 * | 12/2009 | Chen | G01N 35/00732 382/128 |
| 2010/0254788 A1 * | 10/2010 | Dromard | H01L 21/67144 414/222.02 |

* cited by examiner

METHODS AND SYSTEMS FOR CALIBRATION OF A POSITIONAL ORIENTATION BETWEEN A SAMPLE CONTAINER AND NOZZLE TIP

RELATED APPLICATIONS

This application claims priority to U.S. Provisional Application Ser. No. 61/454,293 entitled "METHODS AND SYSTEMS FOR CALIBRATION OF A POSITIONAL ORIENTATION BETWEEN A SAMPLE CONTAINER AND NOZZLE TIP" filed on Mar. 18, 2011, the disclosure of which is hereby incorporated by reference in its entirety herein.

FIELD OF THE INVENTION

The present invention relates generally to methods and systems adapted to calibrate a positional orientation of a nozzle tip to a sample container.

BACKGROUND OF THE INVENTION

In medical testing and processing, the use of robotics may minimize exposure to, or contact with, bodily fluid samples (otherwise referred to as "specimens") and/or may increase productivity. For example, in some automated testing and processing systems (e.g., clinical analyzers) sample containers, such as sample (blood) collection tubes, sample cups, vials, small sample cups (SSCs), and the like, may be transported to and from testing and/or processing systems in sample racks (sometimes also referred to as "cassettes"). The sample racks may contain an array of differently-sized sample containers (e.g., different height sample collection tubes). Furthermore, some or all of the sample collection tubes may include an SSC inserted in a top thereof. SSCs are used when only a small amount of bodily fluid sample has been allocated for a particular process or test. Generally, such SSCs have a much smaller volume-holding capacity than a sample collection tube. A depth and diameter of the SSC are also generally less than the sample container into which they are received. In other embodiments, a sample collection tube may be received in an insert received in a sample rack.

Such transportation of the sample rack may be accomplished by the use of an automated mechanism, which may include a belt or other transportation lane mechanism. The sample rack may be moved from one location to another in relationship to the testing or processing system. At one or more locations along the system, the sample rack may stop, and an image of each sample container in the sample rack may be obtained by an imaging system. At a separate location, an aspiration station, including a moveable aspiration nozzle, may also be provided. At the aspiration station, the nozzle tip of the moveable aspiration nozzle is inserted into the sample container (or SSC) to a desired depth and sample fluid is aspirated therefrom. The sample fluid may then be transferred to another location (e.g., to a cuvette or other reaction vessel) to carry out testing or further processing of the sample fluid thus aspirated.

Although, in general, the location of the nozzle tip in space is theoretically known by a controller of the system, some inaccuracies or deviations from the theoretical position may come into play due to tolerance stack-ups upon system assembly. Such inaccuracies may result in inaccurate positioning of the nozzle tip. This may cause collisions or jams between the nozzle tip and the sample containers or SSCs. Additionally, inaccurate positioning may not allow aspiration of the entire available sample. Furthermore, inaccurate positioning may cause portions of the sample that are undesirable to be aspirated, such as sediment at or very near the bottom of the sample container or SSC. Accordingly, methods and systems that may improve accuracy of positioning of nozzle tips relative to sample containers, especially SSCs, being conveyed to and from testing and processing systems are desired.

SUMMARY OF THE INVENTION

In a method aspect, an improved method of calibrating a position of a nozzle tip relative to a sample container is provided. The method includes providing a nozzle including a nozzle tip; providing a sample rack having a registration location; providing a calibration target (e.g., calibration tool) in the sample rack; positioning the nozzle over the calibration target at a home height location (HM); moving the nozzle downward from the home height location (HM) a distance (D) until a portion of the calibration target is sensed; positioning the nozzle over the sample rack; moving the nozzle downward until a portion of the registration location is sensed to determine a distance (R) from the home height location (HM) to the registration location; imaging the assembly of the sample rack and the calibration target to determine a height (H) between the registration location and a top of the calibration target; and calculating a translation ratio (TR) between the height (H) measured in pixel space and the height (M) measured in machine space, wherein the height (M) is related to the distance (R) and the height (H).

In another method aspect, an improved method of calibrating a position of a nozzle tip relative to a sample container is provided. The method includes providing a moveable nozzle having a nozzle tip; providing a sample rack having a registration location comprising a planar surface feature; providing a sample container in the sample rack having an SSC inserted in the sample container; positioning the nozzle over the SSC at a home position (HM); moving the nozzle downward from the home position (HM) until the nozzle tip contacts a register location comprising a bottom surface of the SSC; determining a distance (D) between the home position (HM) and the bottom surface of the SSC; imaging the planar surface feature of the sample rack and the top surface of the SSC; determining a height (H) from the planar surface feature to a top of the SSC, the height (H) determined in pixel space; and calculating a translation ratio (TR) between the height (H) measured in pixel space and a height (M) measured in machine space, wherein the height (M) is related to the distance (D).

In yet another method aspect, an improved method of calibrating a position of a nozzle tip relative to a sample container is provided. The method includes providing a nozzle including a nozzle tip; providing a sample rack; providing a calibration target in the sample rack; sensing a height (M) between a portion of the calibration target and a registration location, the height (M) measured in machine space; imaging to determine a height (H) between the portion of the calibration target and the registration location, the height (H) measured in pixel space; and calculating a translation ratio (TR) between the height (H) and the height (M).

According to another aspect, an aspiration system is provided. The aspiration system includes a sample rack containing a calibration target, the sample rack or calibration target including a registration location; a robot adapted to move a nozzle having a nozzle tip to sense a portion of the calibration target and the registration location; an imaging apparatus adapted to obtain an image including the registration location and calibration target; and a controller adapted to process the image to determine a height (H) in pixel space between the registration location and a feature on the calibration target, determine a distance (M) in machine space between the registration location and the feature of the calibration target, and calculate a translation ratio (TR) between the height (H) in pixel space and the height (M) in machine space.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

DETAILED DESCRIPTION

As discussed above, in such automated clinical analyzers or processing systems, achieving precision in the placement of a nozzle tip in a sample container (e.g., sample collection tube) is desirable. In particular, if the calibration were inaccurate, then the nozzle may be positioned too close to the bottom of the sample container. Thus, sediment may be aspirated or contact with the bottom may restrict flow/aspiration into the nozzle. However, because tolerance stack-ups due to manufacturing variances and assembly variances of the multitude of connected system components may amount to many thousandths, or many hundredths, or even many tenths of an inch, precise calibration is desired to avoid/minimize the aforementioned problems. Accordingly, means for precisely determining an actual vertical position of a nozzle tip relative to each differently-sized sample container used is desired. This is especially true for systems using SSCs, as the amount of fluid is quite small and the nozzle placement may be required to be more exact than when full-sized sample containers are employed.

In view of the foregoing problems, the present invention provides calibration methods and calibration systems for readily determining an actual position of a nozzle tip such that the nozzle tip may be precisely located at a predetermined location in a sample container during aspiration.

In a first aspect, a method of calibrating a position of a nozzle tip relative to a sample container is provided. The method includes providing a moveable nozzle including a nozzle tip, providing a sample rack having a registration location, providing a calibration target (e.g., sample container, SSC, or a calibration tool) in the sample rack, determining a distance (D) to a portion of the calibration target (e.g., top or bottom), imaging the assembly of the sample rack and the calibration target to determine a height (H) in pixel space between the registration location and a top of the calibration target, and calculating a translation ratio (TR) based on the height (H) measured in pixel space and the distance (D) measured in machine space. The distance (M) is related to the distance (D) in machine space, where TR=M/H. The translation ratio (TR), once determined, may be used to drive the nozzle tip to a desired depth in any sample container.

In another aspect, a method of calibrating a position of a nozzle tip relative to a sample container is provided. The method includes providing a moveable nozzle including a nozzle tip, a sample rack having a registration location, and a calibration target (e.g., sample container, SSC, or calibration tool) in the sample rack, the calibration target having a label affixed thereon. A distance (D) to a portion of the calibration target (top) is determined based upon an image of the label, and an image of the assembly of the sample rack and the calibration target is used to determine a height (H) in pixel space between the registration location and a top of the calibration target. A translation ratio (TR) is then calibrated between the height (H) measured in pixel space and the distance (D).

These and other aspects and features of the invention will be described with reference to FIGS. 1-7 herein.

In accordance with a first embodiment of the invention, as best shown in FIGS. 1 and 2A-2F, an aspiration system 100 that is robotically controlled is shown. The aspiration system 100 is useful for precisely aspirating a sample fluid from one or more sample containers 102A-102E contained or held in a sample rack 105. The sample containers 102A-102E may be of various sizes (e.g., small, medium, tall), and some containers may be SSCs (e.g., 102A, 102D, and 102E)

inserted in sample collection tubes, for example. A nozzle 104 including a lower nozzle tip 104A is positioned in use by a robot 106 for aspiration of sample fluid from the sample containers 102A-102E. Although the nozzle is shown with a removable tip component, single-piece nozzles may be used as well. In some embodiments, vertical and/or horizontal motions of the nozzle 104 may be controlled by the robot 106 and a controller 108. The robot 106 may be provided in any suitable orientation relative to the sample rack 105, such that a sample fluid (not shown) contained in the sample containers 102A-102E may be aspirated and transferred to another location (e.g., to a cuvette or other reaction vessel) for further processing or testing.

Figure 1:
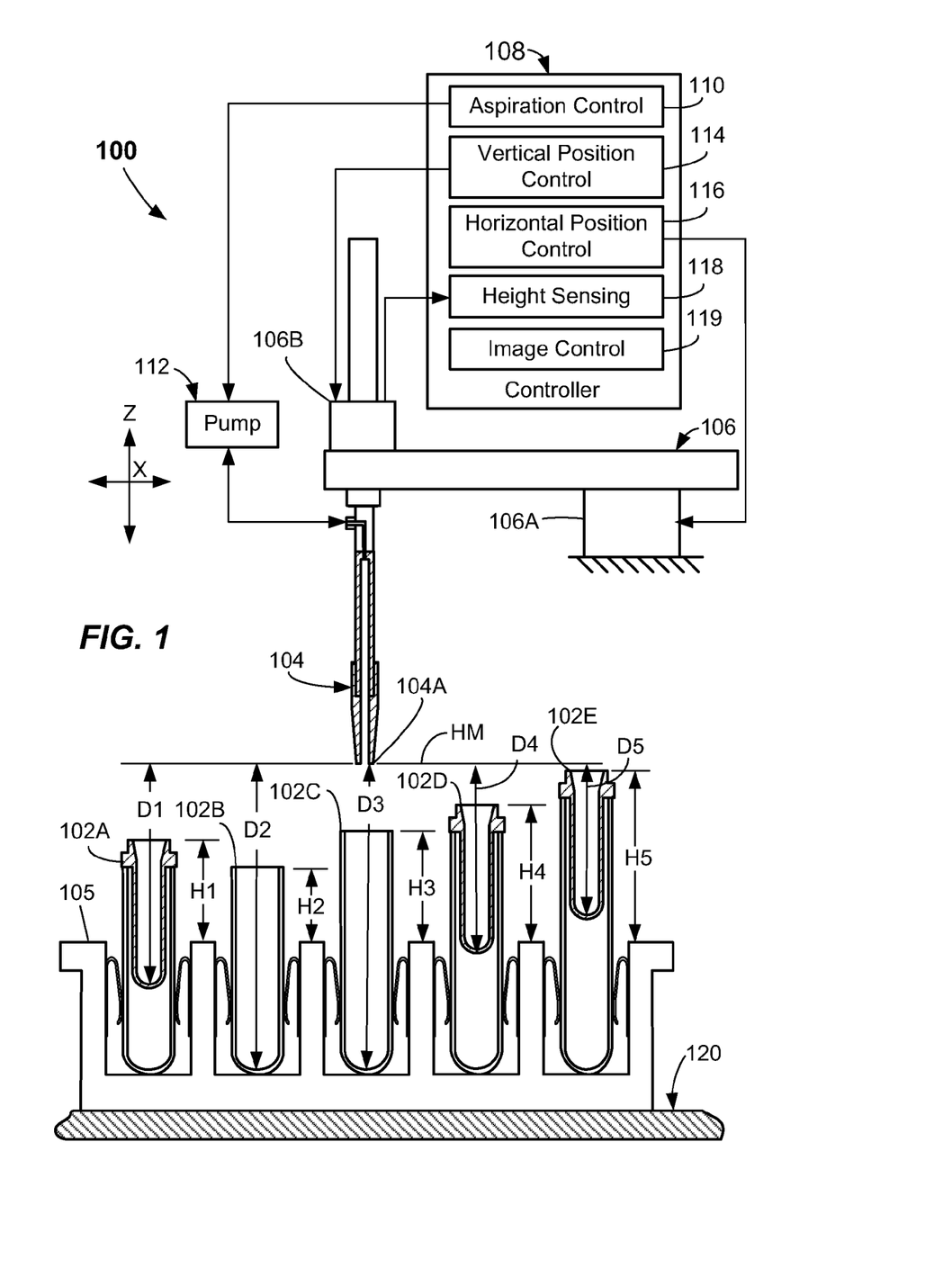
FIG. 1 is a partially-cross sectioned side view illustration of an exemplary robotic system including a nozzle whose orientation is calibrated according to embodiments of the invention.

As shown in FIG. 1, the nozzle 104 is moveable in the X and Z directions, for example. The robot 106 may include other degrees of freedom (e.g., X, Y, and Z). The controller 108 may command the robot 106 and attached nozzle 104 and move the nozzle 104 in one or more coordinate directions, or two or more coordinate directions. Any suitable robot 106 may be used, such as a moveable robot arm, boom, or beam having the nozzle 104 coupled thereto. In some embodiments, the robot 106 may include one or more shoulder, elbow, or wrist elements to accomplish two-dimensional or three-dimensional motion of the nozzle 104.

In other embodiments, the robot 106 may include a frame and a moveable gantry arrangement with the nozzle 104 being mounted to a boom. The boom may be moveable (e.g., in the X direction) on a suitable track, slide, worm drive, or guide mechanism by suitable motor 106A. Furthermore, the boom (and the nozzle 104) may be moveable along one or more additional tracks, slides, or guides in an additional direction (e.g., the Y direction). Vertical motion of the nozzle 104 in the Z direction relative to the boom may be accomplished by a vertical motor 106B. The means for moving the robot 106 in the various coordinate directions may include any suitable number of conventional motion-producing mechanisms, such as one or more stepper motors, servo motors, pneumatic or hydraulic motors, electric motors, etc. Furthermore, drive systems including chains, guides, pulleys and belt arrangements, drives such as gear or worm drives, or other conventional drive components may be utilized to cause the motion of the robotic component 106 and coupled nozzle 104. Other suitable types of robots may be employed.

The aspiration system 100 depicted may be a part of a biological testing system, such as a clinical chemical analyzer, adapted to aspirate a portion of a sample biological fluid contained in the sample container and transport the sample fluid to another location for testing or further processing.

Again referring to FIG. 1, the nozzle 104 may be aligned horizontally (in the X direction) by drive motor 106A with the desired sample container 102A-102E and driven along the Z direction by the drive motor 106B, such as a stepper motor or other drive motor. For illustration purposes, the aspiration system 100 is shown configured as an X-Z robot. However, it should be recognized that the robot 106 may be rotated 90 degrees and configured as an X-Y-Z robot, where the X dimension is used to position the nozzle 104 into and out of the paper, the Y dimension locates the nozzle 104 along the length of the sample rack 105, and the Z dimension moves the nozzle 104 vertically. Other arrangements may be used. Furthermore, a transportation lane 120 may cause the positioning of the sample rack 105 in the X direction.

The controller 108 of the system 100 includes an aspiration control 110 to enable the nozzle 104 to aspirate a suitable portion of the fluid sample contained in the sample container during testing (after calibration). Any suitable pump 112 and controls may be used to aspirate the fluid sample. For example, the aspiration system described in U.S. Pat. No. 7,867,769 may be used. Vertical position control 114 and horizontal position control 116 may be provided to accomplish appropriate motions of the nozzle 104 during aspiration as well as motions during execution of a calibration method.

Suitable feedback mechanism(s), sensing, or sensor(s) may be provided such that feedback information of a position of the robot 106 and, thus, the nozzle tip 104A in coordinate space is provided. Height sensing 118 may be provided. Height sensing 118 is adapted to indicate the height of any object that the nozzle tip 104A comes into contact with. For example, in some embodiments, the height sensing 118 may comprise a suitable electrical circuit monitoring a load current of the vertical motor 106B and indicating a contact with an article in the Z direction. The monitoring of the electrical current may indicate contact with an article when the current exceeds a predetermined threshold level, i.e., signifying an increasing load on the vertical motor 106B. In other embodiments, if the nozzle 104 includes capacitive level sensing capability, then the height sensing 118 may be used in conjunction with a capacitive sensor of the nozzle 104 to detect height. For example, if capacitive level sensing capability is used to provide height sensing 118, then a calibration target used by the calibration method may be a calibration tool, which may be electrically conductive. In other embodiments, where load control is monitored as part of the height sensing 118, the calibration target may be a sample container, such as a sample collection tube or a SSC.

In the depicted embodiment of FIG. 1, the sample rack 105 is shown positioned at an aspiration station, i.e., a location where aspiration of sample fluids from sample containers 102A-102E is adapted to take place. The sample rack 105 may be transported to the aspiration location by any suitable transportation mechanism 120, such as a transportation lane including a driven belt onto which the sample rack 105 is placed. Other transport mechanisms, such as robots, may be used.

Figure 2A:
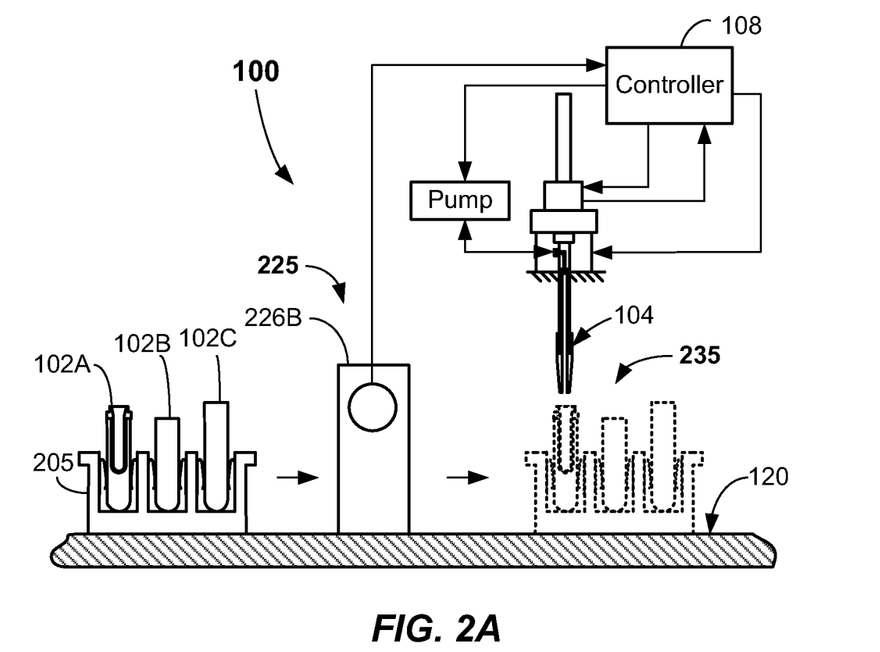
FIG. 2A is a side view graphical depiction that illustrates various rack positions or stations of the sample rack during calibration according to embodiments of the invention.
Figure 2B:
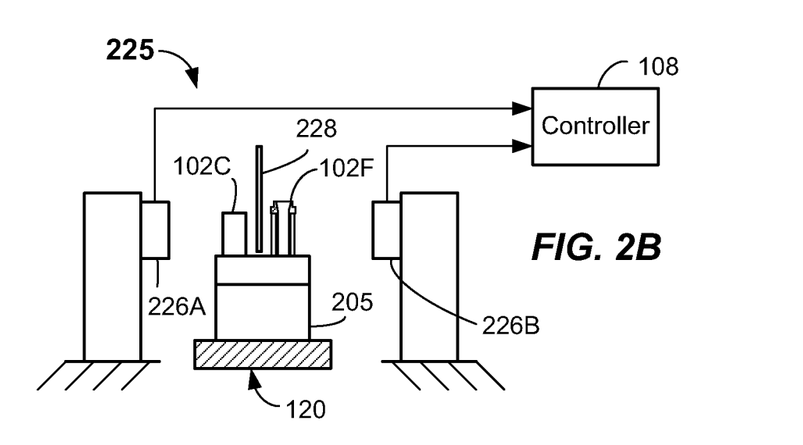
FIG. 2B is a side view graphical depiction that illustrates a sample rack at an imaging station during calibration according to embodiments of the invention.

In more detail, the aspiration system 100, as shown in FIGS. 2A and 2B, includes an imaging station 225 adapted to image at least a portion of a sample rack 205 and at least one of the calibration targets (e.g., sample containers 102A-102F) contained or held therein, and an aspiration station 235 adapted to aspirate a sample fluid from a sample container (e.g., 102A-102F) in use. Although a six position (2×3) sample rack 205 is shown in FIGS. 2A-3 and 5-7, the present invention will work with any sized sample rack where an image of the calibration targets (sample containers) housed therein may be obtained. In the depicted embodiment, one or more imaging apparatus 226A, 226B, such as digital cameras, may be used to obtain an image of one or more calibration targets (e.g., sample containers 102A-102F) in the sample rack 205 and portions of the sample rack 205.

Figure 2C:
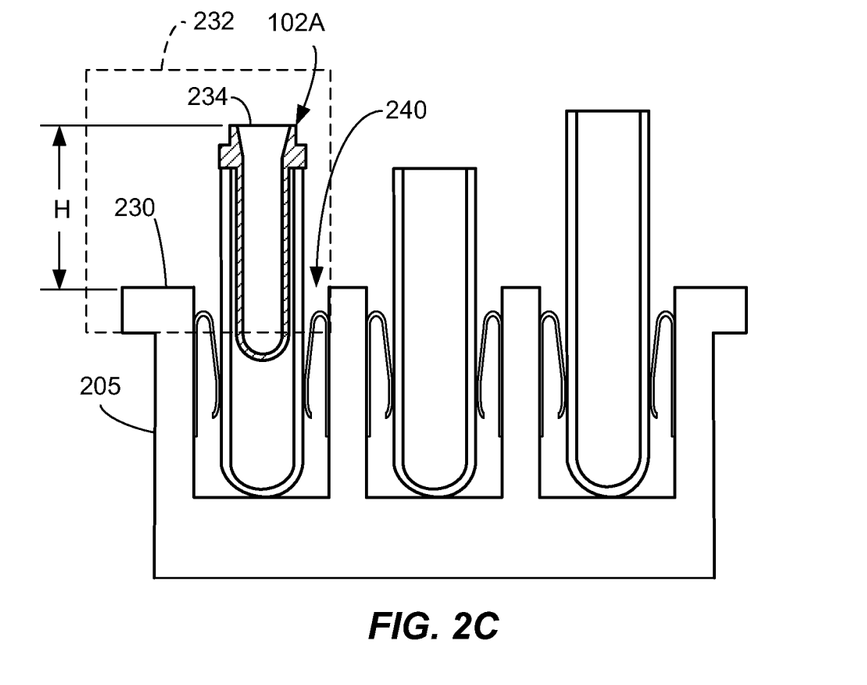
FIGS. 2C and 2D are partially cross-sectioned side view graphical depictions that illustrate an imaging window of a sample rack and calibration target taken at an imaging station during calibration according to embodiments of the invention.
Figure 2D:
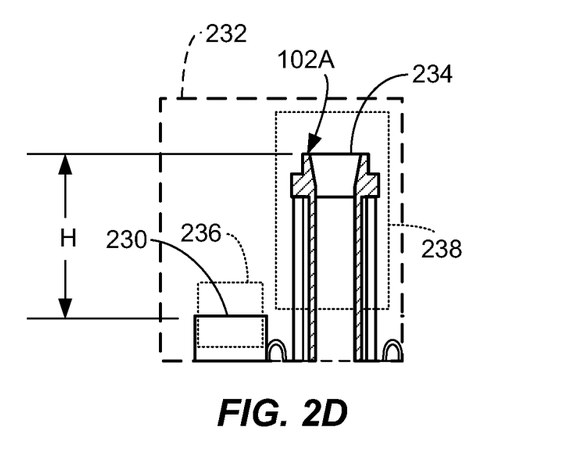

The transportation apparatus 120 is able to stop the sample rack 205 with sufficient precision so that the sample rack 205 with a first calibration target 102A (and 102D if two cameras are used) stops directly in front of the camera 226A (and 226B if two cameras are used). In the embodiment shown, a divider 228 is provided at an orientation between the sample containers (e.g., 102A-102C) located on a first side of the rack 205 and the containers located on the second side of the rack 205 (e.g., 102D-102F). The divider 228 may be a dual-sided mirror, for example. Other suitable dividers may be used to isolate the image taken to only the calibration target on that particular side of the divider 228. The imaging apparatus 226A, 226B obtains an image 232 (e.g., a digital image) of the sample rack 205 and the calibration target (e.g., sample container 102A) (as shown in FIGS. 2C-2D) at the imaging station 225 (shown in FIGS. 2A-2B). That image 232 is sent to the image control 119 of the controller 108 (FIG. 1) for further processing.

The processing of the image 232, as best shown in FIGS. 2C and 2D, includes locating within the image 232, a registration location 230 on the sample rack 205 and a location of a top 234 of the calibration target 102A. The registration location 230 may include a line within a certain smaller pixel window 236 of the image 232. In practical implementation, the registration location 230 may be any surface feature that may be readily imaged and identified, such as a substantially planar horizontal surface provided directly proximate to a receptacle 240 of the sample rack 205. Additionally, the image processing routine identifies the top surface 234, again by searching for a line at an uppermost extent within a smaller pixel window 238 in the image 232. Then, the image processing routine determines a height (H) between the registration location 230 and the top 234 of the calibration target 102A in pixel space. This may be accomplished for only one, or for all of the calibration targets (e.g., sample containers 102A-102F) in the sample rack 205. An image 232 should be taken for at least one calibration target (e.g., 102A, 102D) on each side of the rack 205, when a two row sample rack (as shown in FIGS. 2A-3 and 5-7) is used. The measurement (H) may be determined and recorded in memory in pixel space, i.e. it may be measured in pixels. For example, the measured height (H) may be stored as about 160 pixels. Other values may be measured, depending on the size of the sample container 102A-102F. Additionally, the imaging routine may analyze the shape of a top of the calibration target (e.g., sample container 102A) and look for a geometrical feature or features to aid in determining if the sample container is a standard sample container (e.g., blood collection tube) or an SSC. For example, the imaging routine may search for a geometrical feature, such as a flange or a notch, which, if present, signifies that the sample container is an SSC. If devoid of the feature, the sample container is a standard sample container. Alternatively, imaging software may compare the image to a library of images of all known possibilities stored in memory, and determine whether an SSC is present and determine the height of sample container.

Once a first imaging at the imaging station 225 is completed, the transportation lane 120 may transport the sample rack 205 and calibration target(s) to an aspiration station 235 located underneath the moveable nozzle 104. In some embodiments, the imaging and aspiration stations may be co-located.

Figure 2E:
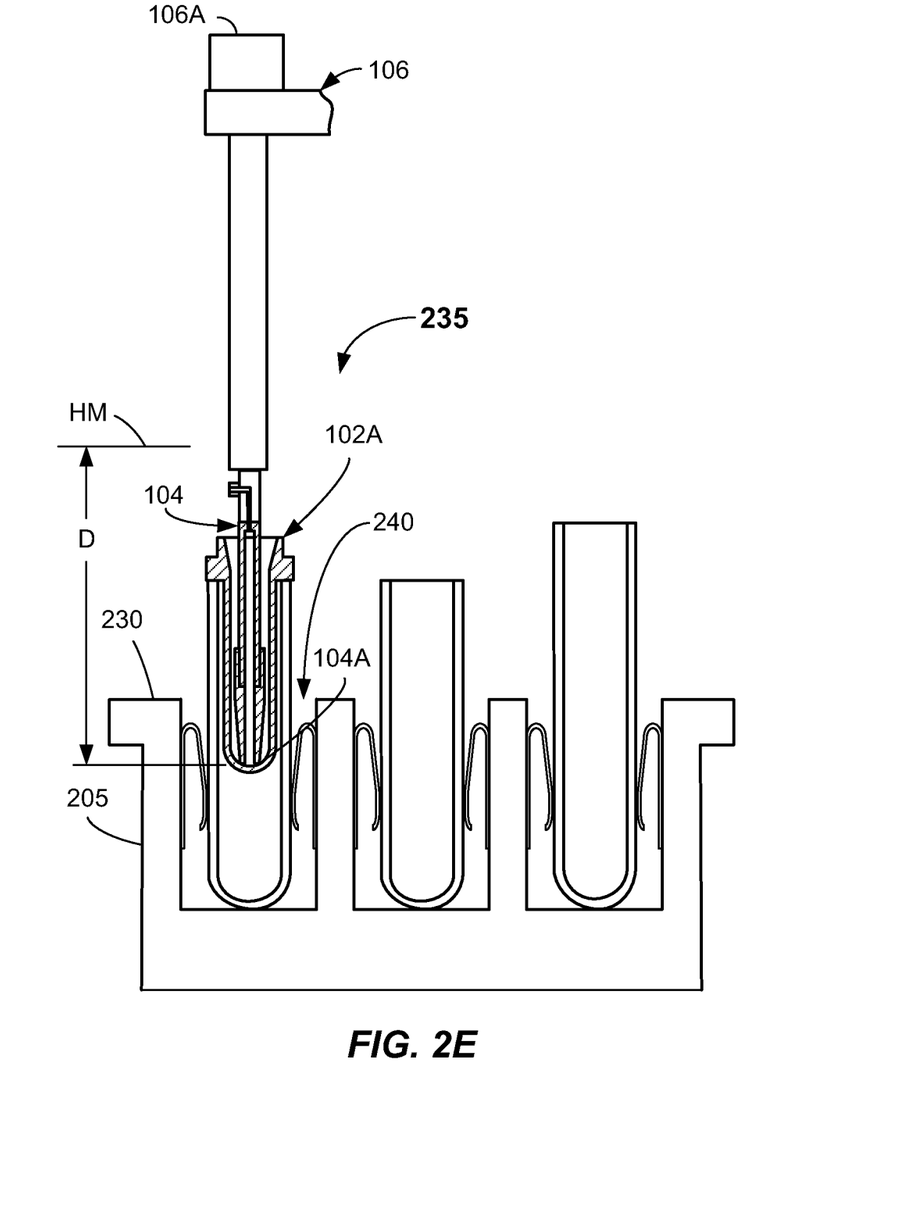
FIG. 2E is a partially cross-sectioned side view graphical depiction that illustrates a nozzle tip contacting a calibration target during a calibration method according to embodiments of the invention.

As shown in FIG. 2E, after being positioned over the calibration target 102A at a home height location (HM), the nozzle 104 is moved downward by drive motor 106A from the home height location (HM) until a portion of the calibration target (e.g., bottom) is sensed, as shown. The sensing may occur when the nozzle tip 104A contacts a portion of the calibration target 102A (e.g., the bottom) and an increased current above a threshold is noted. This distance (D) from the home height position (HM) to the bottom of the calibration target 102A may be recorded in memory. The distance (D) may be recorded in machine space, using any suitable measure. For example, if a stepper motor is used at the vertical drive motor 106A, then the distance (D) may be recorded as a number of steps (S) from the home height location (HM) until the portion of the calibration target 102A is sensed. In optional embodiments, a top of a calibration target (e.g., a calibration tool) may be sensed.

Figure 2F:
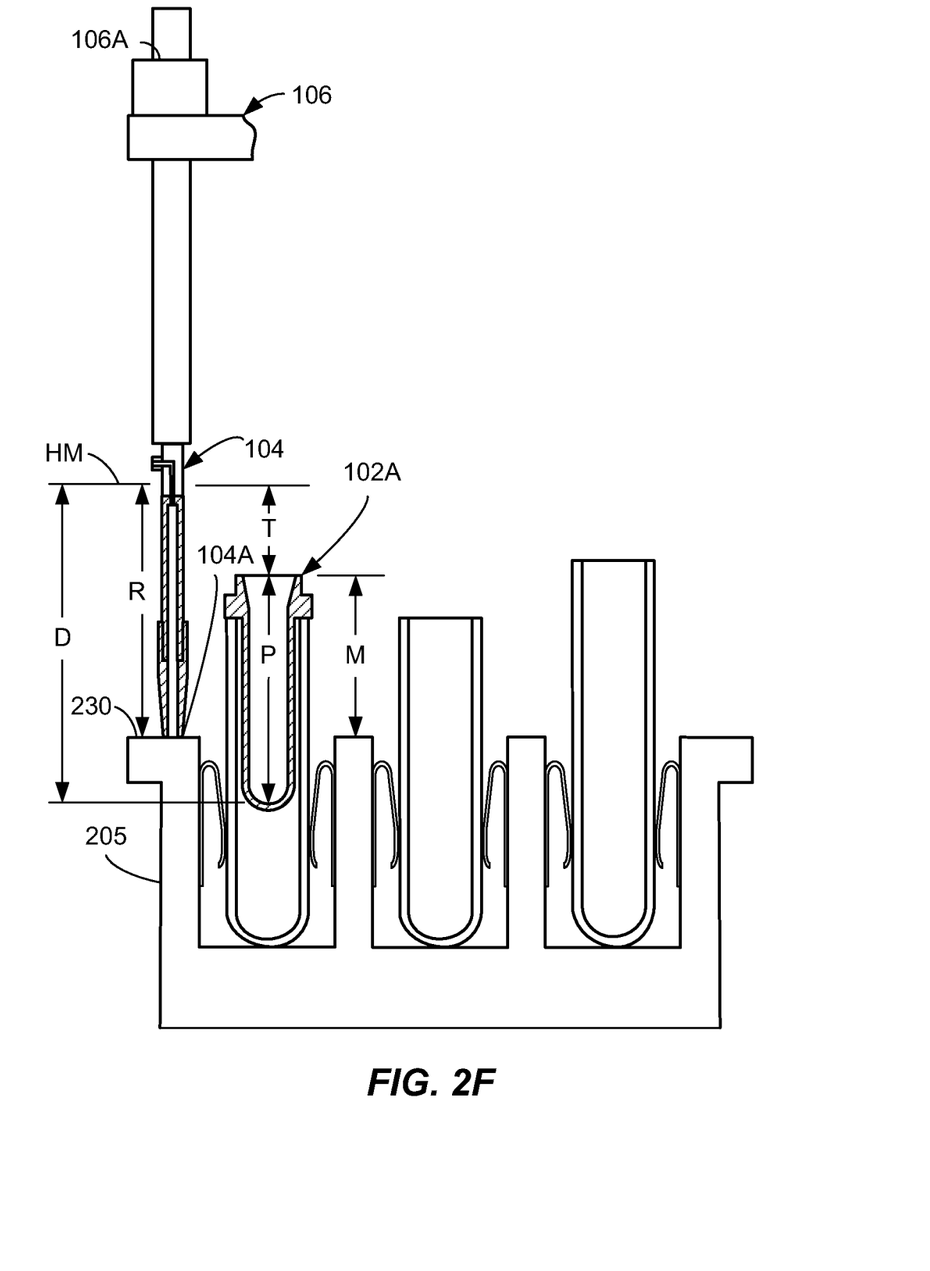
FIG. 2F is a partially cross-sectioned side view graphical depiction that illustrates a nozzle tip contacting a registration location of a sample rack during a calibration method according to embodiments of the invention.

According to the calibration method, the nozzle 104 is also positioned over the sample rack 205 and the nozzle 104 is moved downward until a portion of the registration location 230 is sensed as is shown in FIG. 2F. Accordingly, a distance (R) between the home height location (HM) and the registration location 230 may be determined. The distance (R) may be recorded in machine space, using the same measure as for distance (D). The order of measurement of the registration location 230 and the portion of the calibration target 102A may be in any order. The sensing may be by the nozzle 104, in a first instance, by sensing a load current of the drive motor 106A. When the load current exceeds a threshold, then contact with the bottom is indicated. Optionally, if the nozzle has capacitance measuring capability, then the contact may be sensed with the calibration target using a capacitance measuring circuit. In this case, the calibration target will be a conductive tool. For example, the calibration target may be a tool made of steel that has the same dimensions as a blood collection tube or of an SSC.

The imaging operation and the height sensing operation of the calibration method may be determined in any order. However, it is preferred that the height measurement take place first, as the contact with the nozzle tip 104A will ensure that the calibration target is properly seated in the sample rack 205 (in contact with a bottom surface thereof). Additionally, in some embodiments, an imaging step may be undertaken initially to determine a type of sample container used, the height measurement steps undertaken, followed by another imaging step to determine the height in pixel space.

Once the height (H) measured in pixel space and the height (M) in machine space are determined, a translation ratio (TR) may be calculated according to an aspect of the method. The translation ratio (TR) is defined in Equation 1:

$$TR = M/H \qquad \text{Equation 1}$$

wherein (H) is the measured height from the imaging step in pixel space, and M is, in the FIG. 2F embodiment, expressed as shown in Equation 2:

$$M = R - T \qquad \text{Equation 2}$$

wherein T is the distance from the home height position (HM) to a top of the calibration target 102A and is expressed as in Equation 3:

$$T = D - P \qquad \text{Equation 3}$$

wherein D is the height in machine space between the home height location (HM) and the bottom of the calibration target 102A, and wherein P is the known height from the bottom of the SSC to the top of the SSC.

Figure 3:
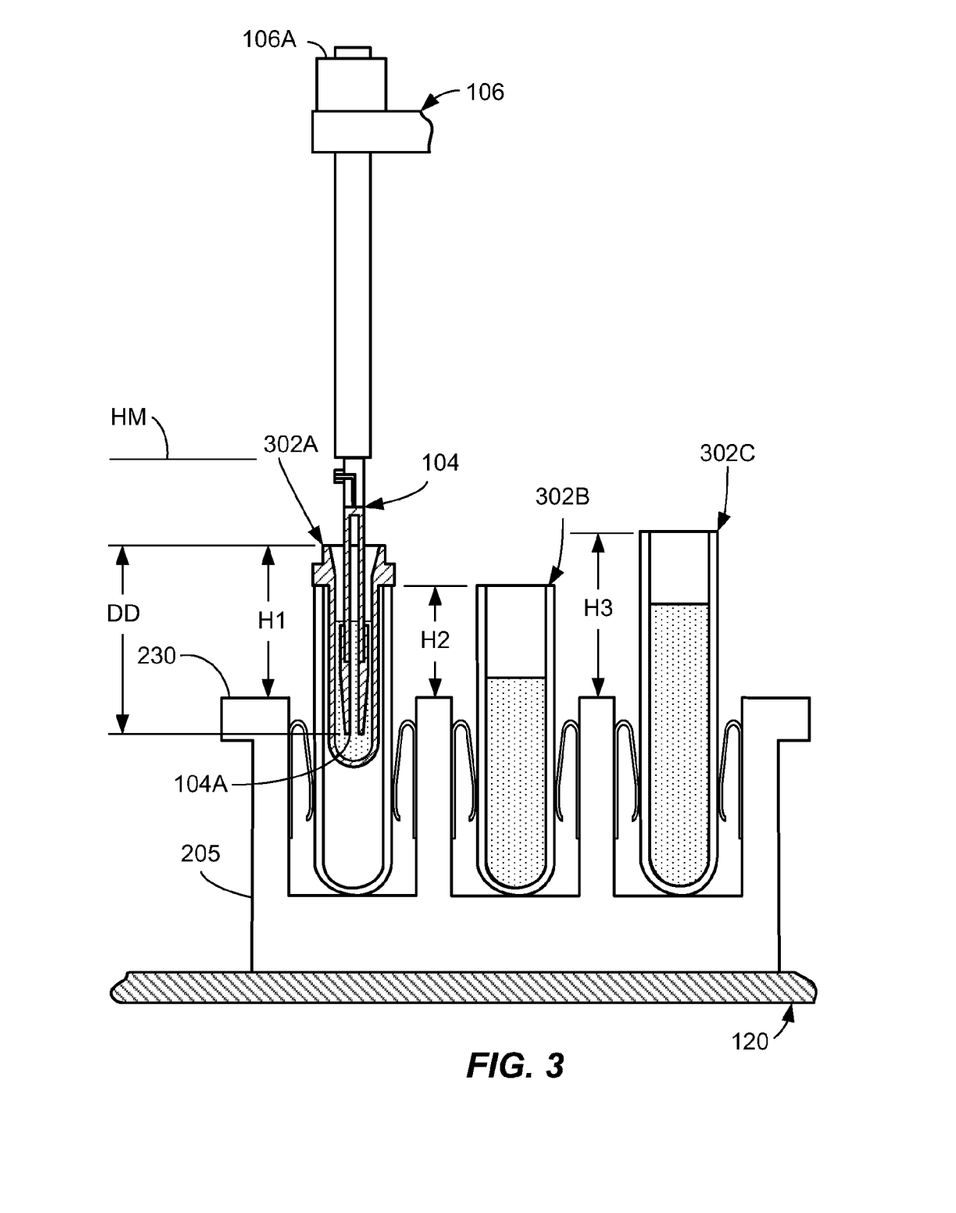
FIG. 3 is a partially cross-sectioned side view graphical depiction that illustrates a nozzle tip being driven to a predefined depth in a sample container by using the translation ratio (TR) obtained by the calibration method of the invention.

Now referring to FIG. 3, once the calibration routine is completed resulting in the determination of the translation ratio (TR) between the pixel space and machine space, the translation ratio (TR) may be used to drive the nozzle 104 to a desired drive depth (DD) in each sample container 302A-302C contained in the sample rack 205 in use. For example, after the calibration method is completed, and in normal operation, a sample rack 205 with sample containers 302A-302C therein is provided at the previously-described imaging station 225 by the transportation lane 120. Only three sample containers are shown for clarity. However, it should be understood that three additional containers (e.g., 302D-302F) of any height or configuration may be provided on the other half of the sample rack 205. The cameras 226A, 226B capture images of each of the sample containers 320A-302C one by one. These images are processed, as before, to determine a height (H1) between the top of each sample container 302A-302C and the registration location 230 on the sample rack 205 directly adjacent to the respective sample container, in the same manner as shown in FIG. 1. These height values (H1 to H3) are stored in memory and compared to values of known sample containers (e.g., 13×75 mm, 16×75, 15×92 mm, 13×100 mm, 15×100 mm). Additionally, the geometry of the top is analyzed for geometric features that indicate the presence of an SSC in a sample collection tube. The height values (e.g., H1) plus the geometry information on the top of the container (e.g., 302A) are used to determine the presence of an SSC and what size sample collection tube it has been placed into.

Based on these imaged height values (H1-H3) in pixel space and whether an SSC is contained therein, the routine then uses the translation ratio (TR) to drive the nozzle tip 104A to the desired depth (D) in the sample container 302A-302C. For each type of sample container 302A-302C there will be a desired predetermined stored drive depth (DD) in software that the nozzle tip 104A should be driven to. For example, the drive depth (DD) may be approximately 90% of the distance (P) between the top and bottom of the sample container or SSC such that sediment is not aspirated, and/or so that utilization of the sample is improved. For example, the following Equation 4 explains how the translation ratio (TR) is used. First, the nozzle tip 104A may be driven to the location of the top of the sample container 302A-302C designated by:

$$\text{Top of container} = R - M \qquad \text{Equation 4A}$$

$$DD = P \times 0.9 \qquad \text{Equation 4B}$$

Thus, simply imaging the sample containers and using the translation ratio (TR) and previously-obtained information about the location of the tip 104A relative to the sample rack 205 (see FIG. 2E), the nozzle tip 104A may be driven to the desired drive depth (DD) very precisely. This is because an accurate translation between image space in pixels to machine space has been previously made during the calibration. In some embodiments, the drive depth (DD) may be provided as a number of steps of a stepper motor driving the vertical location of the nozzle 104. The value of 0.9 used above is exemplary only; the nozzle tip 104A may be driven to any desirable fraction of the distance (P) (e.g., 0.75, 0.8, 0.85, 0.9, 0.95, etc.).

Figure 4:
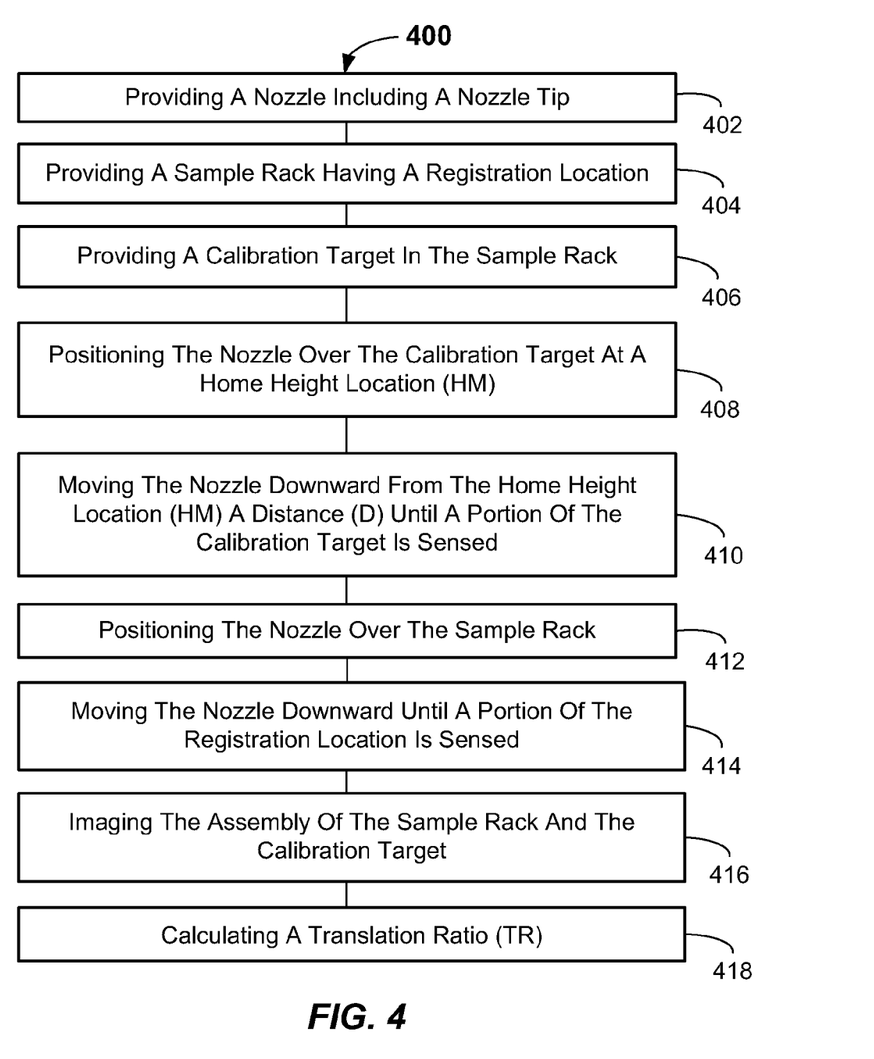
FIG. 4 is a flowchart illustrating a method according to embodiments of the present invention.

A method of calibrating a position of a nozzle tip relative to a sample container of the invention will now be explained with reference to FIG. 4. The method 400 includes providing a nozzle including a nozzle tip in 402, providing a sample rack having a registration location in 404, and providing a calibration target in the sample rack in 406. The calibration target may be a sample container, SSC, or calibration tool. In step 408, the nozzle is positioned over the calibration target at a home height location (HM), and moved downward in 410 from the home height location (HM) a distance (D) until a portion of the calibration target is sensed. The top or bottom of the calibration target may be sensed. The nozzle is moved and positioned over the sample rack in 412. The nozzle is moved downward until a portion of the registration location is sensed in 414 to determine a distance (R) from the home height location (HM) to the registration location. From these sensing steps, the locations in machine space (e.g., in a number of steps of a stepper motor) may be determined and stored in memory. In 416, an image (e.g., a digital image) of the assembly of the sample rack and the calibration target are obtained to determine a height (H) between the registration location and a top of the calibration target. This height (H) is in pixel space. In 418, a translation ratio (TR) is calculated. The translation ratio (TR) is a ratio between the height (H) measured in pixel space and the height (M) measured in machine space. (M) is related to distance (R) and height (H) as described above.

Figure 5:
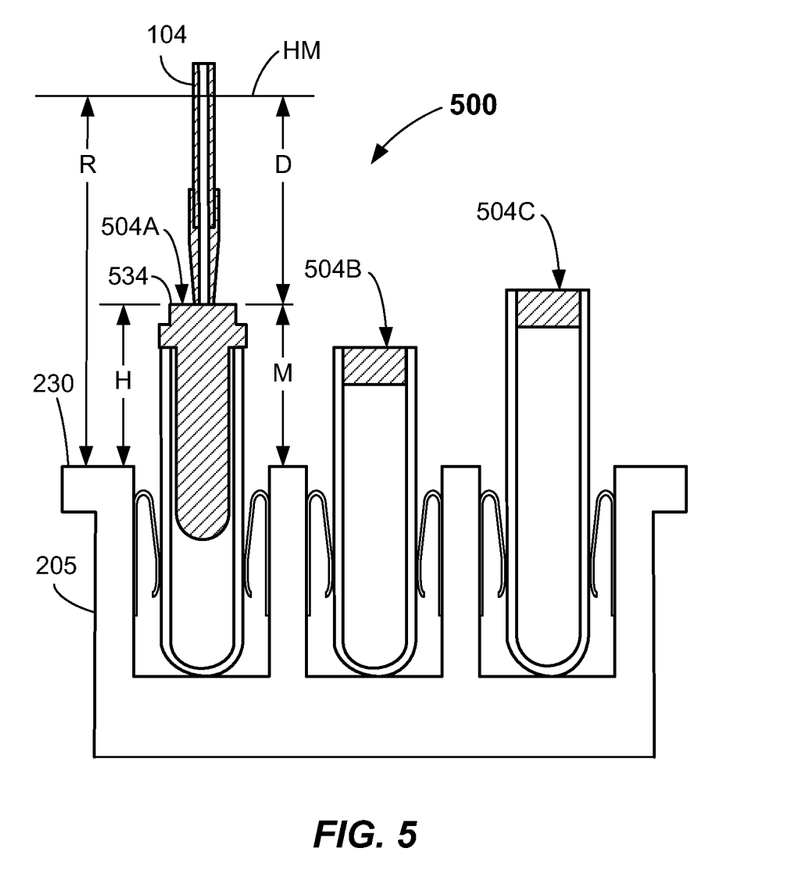
FIG. 5 is a partially cross-sectioned, side view graphical depiction that illustrates using one or more calibration tools according to embodiments of the invention.

FIG. 5 illustrates an alternative system 500 adapted to aid in calibrating a position of a nozzle tip of a nozzle 104 relative to a sample container of the invention. In this method and system, a calibration tool 504A is used as the calibration target. In this embodiment, the nozzle 104 is moved downward from the home height location (HM) a distance (D) until a top portion 534 of the calibration target (e.g., calibration tool 504A) is sensed. Additionally, R is sensed as previously described. Height (M) in machine space is then calculated by Equation 5 below.

$$M = R - D \qquad \text{Equation 5}$$

The imaging of the assembly of the sample rack and the calibration target to determine a height (H) between the registration location and a top of the calibration target in pixel space is performed as previously described. The translation ratio (TR) may then be calculated. One or more additional calibration of tools 504B, 504C may also take place. However, it should be understood that only one calibration per camera need take place. Calibrating the additional calibration targets of different sizes may increase the accuracy of the calibration.

Figure 6:
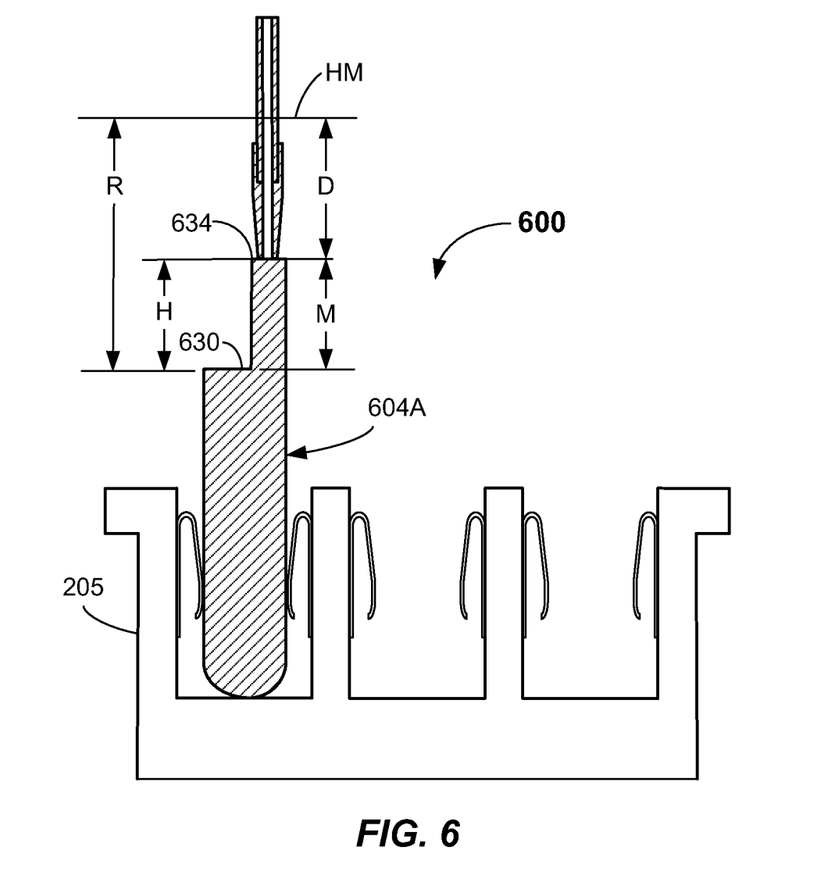
FIG. 6 is a partially cross-sectioned, side view graphical depiction that illustrates using another embodiment of a calibration tool according to embodiments of the invention.

FIG. 6 illustrates another alternative system 600 adapted to aid in calibrating a position of a nozzle tip of a nozzle 104 relative to a sample container of the invention. Only the nozzle is shown with the robot and controller not shown for clarity. In this method and system, a calibration tool 604A is used as the calibration target wherein the calibration tool 604A is contained in a sample rack 205 in a known orientation. In this embodiment, the nozzle 104 is moved downward from a home height location (HM) a distance (D) until a feature (e.g., a top portion 634) of the calibration target (e.g., calibration tool 604A) is sensed. Additionally, a distance (R) to the registration location 630 of the calibration tool 604A from the home height location (HM) is sensed. Sensing may be by the aforementioned load sensing or by sensing capacitance (where the tool 604A will be made of a conductive metal). Height (M) in machine space is then calculated and determined by Equation 5 above.

Furthermore, an image is obtained including the registration location 630 and feature (e.g., top 634) of the calibration target 604A. The image may be obtained using the imaging station 225 such as previously described in FIG. 2B. From the image, the controller 108 processes the image to determine a height (H) between the registration location 630 and the feature (e.g., top 634) of the calibration target 602A in pixel space. The translation ratio (TR) between the height (H) measured in pixel space and the height (M) measured in machine space may then be calculated by the controller. One or more additional calibration tools may be included in the sample rack 205 and calibration thereof may also take place.

Figure 7:
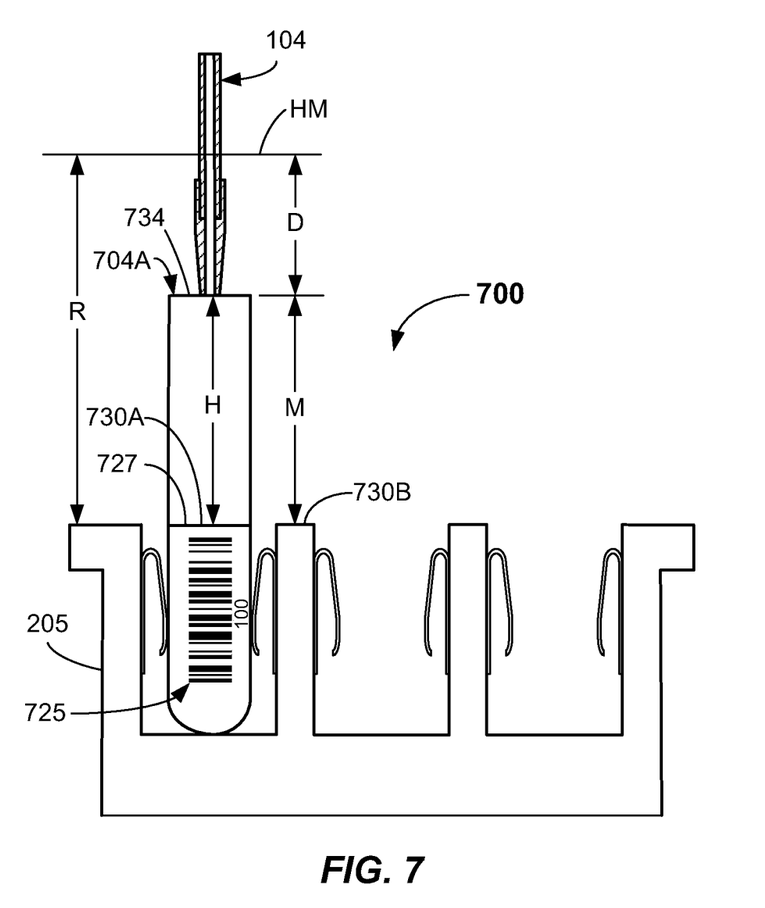
FIG. 7 is a partially cross-sectioned, side view graphical depiction that illustrates using another embodiment of a calibration tool according to embodiments of the invention.

FIG. 7 illustrates another alternative system 700 adapted to aid in calibrating a position of a nozzle tip of a nozzle 104 relative to a sample container of the invention. Only the nozzle 104 is shown with the robot and controller not shown for clarity. In this method and system 700, a calibration tool 704A is used as the calibration target wherein the calibration tool 704A is contained in a sample rack 205 in a known orientation. In this embodiment, the calibration tool 704A includes a barcode 725 provided on a surface thereof. The barcode 725 may be readable at the imaging station 225 (FIG. 2B). The calibration tool 704A includes a line 727 at a height from the top surface 734 of the tool 704A that is precisely known. The line 727 is provided at the registration location 730A, which in this embodiment is at the same height as the upper planar surface 730B of the sample rack 205. Thus, sensing the line 730A, senses the registration location 730B. In this embodiment, the nozzle 104 is moved downward from a home height location (HM) a distance (D) until a feature (e.g., a top surface 734) of the calibration target (e.g., calibration tool 704A) is sensed. Additionally, a distance (R) to the line 730A of the calibration tool 704A from the home height location (HM) is sensed via sensing registration location 730B. Sensing may be by the aforementioned load sensing. Height (M) in machine space is calculated and determined by Equation 5 above.

Furthermore, an image is obtained including the registration location 730A and feature (e.g., top surface 734) of the calibration target 704A. The image may be obtained using the imaging station 225 as previously described in FIG. 2B. The controller 108 processes the image to determine a height (H) between the registration location 730A (the line 727) and the feature (e.g., top surface 734) of the calibration target 704A in pixel space. The translation ratio (TR) between the height (H) measured in pixel space and the height (M) measured in machine space may be calculated by the controller. One or more additional calibration tools may be included in the sample rack 205 and calibration thereof may also take place.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the scope of the invention.

What is claimed is:

1. A method of calibrating a position of a nozzle tip relative to a sample container, comprising:
    providing a nozzle including a nozzle tip, the nozzle operably configured to aspirate a sample fluid from the sample container;
    providing a sample rack having a receptacle configured to contain the sample container during the aspirate the sample rack having a registration location;
    inserting a calibration target in the receptacle of the sample rack;
    positioning the nozzle over the calibration target at a home height location (HM);
    moving the nozzle downward from the home height location (HM) a distance (D) until a portion of the calibration target is sensed;
    positioning the nozzle over the sample rack;
    moving the nozzle downward until a portion of the registration location of the sample rack is sensed to determine a distance (R) from the home height location (HM) to the registration location;
    imaging the assembly of the sample rack and the calibration target to determine a height (H) between the registration location and a top of the calibration target in pixel space; and
    calculating a translation ratio (TR) between the height (H) measured in the pixel space and the height (M) measured in machine space, wherein (M) is related to distance (R) and height (H);
    wherein each of distance (D) and distance (R) is measured in a number of steps (S) of a stepper motor;
    the method further comprising: generating the translation ratio (TR) between the number of steps (S) and the height (H); and
    using the translation ratio (TR) to drive the nozzle tip to a predetermined drive depth (DD) in a sample container.

2. The method of calibrating of claim 1, wherein the sensed portion of the calibration target is a bottom of a sample collection tube or small sample cup (SSC).

3. The method of calibrating of claim 1, wherein the sensed portion of the calibration target is a top of a calibration tool.

4. The method of calibrating of claim 1, wherein the registration location comprises a planar surface feature on the sample rack.

5. The method of calibrating of claim 1, wherein the registration location comprises a planar surface feature on the sample rack directly proximate to the calibration target.

6. A method of calibrating a position of a nozzle tip relative to a sample container, comprising:
    providing a nozzle including a nozzle tip, the nozzle operably configured to aspirate a sample fluid from the sample container;
    providing a sample rack having a receptacle configured to contain the sample container during the aspirate the sample rack having a registration location;
    inserting a calibration target in the receptacle of the sample rack;
    positioning the nozzle over the calibration target at a home height location (HM);
    moving the nozzle downward from the home height location (HM) a distance (D) until a portion of the calibration target is sensed;
    positioning the nozzle over the sample rack;
    moving the nozzle downward until a portion of the registration location of the sample rack is sensed to determine a distance (R) from the home height location (HM) to the registration location;
    imaging the assembly of the sample rack and the calibration target to determine a height (H) between the registration location and a top of the calibration target in pixel space; and
    calculating a translation ratio (TR) between the height (H) measured in the pixel space and the height (M) measured in machine space, wherein (M) is related to distance (R) and height (H);
    the method further comprising, after calibration, imaging a sample container to determine an imaged height of the sample container, and
    multiplying the imaged height (IH) by the translation ratio (TR) and a factor to obtain a drive distance to drive the nozzle tip in machine space.

7. The method of calibrating of claim 1, wherein the calibration target is a calibration tool.

8. The method of calibrating of claim 7, wherein the calibration tool is electrically conductive, and the distance (D) is determined by sensing a conductive surface of the calibration tool.

9. The method of calibrating of claim 8, wherein the distance (D) is determined by sensing a load of a drive motor used to drive the nozzle in a Z direction.

10. A method of calibrating a position of a nozzle relative to a sample container, comprising:

providing a moveable nozzle having a nozzle tip, the moveable nozzle operably configured to aspirate a specimen;

providing a sample rack having a receptacle and a registration location comprising a planar surface feature;

providing a sample container inserted in the receptacle of the sample rack having a small sample cup (SSC) inserted in the sample container;

positioning the nozzle over the SSC at a home position (HM);

moving the nozzle downward from the home position (HM) until the nozzle tip contacts a register location comprising a bottom surface of the SSC;

determining a distance (D) between the home position (HM) and the bottom surface of the SSC;

imaging the planar surface feature of the sample rack and the top surface of the SSC;

determining a height (H) from the planar surface feature to a top of the SSC, the height (H) determined in pixel space;

and calculating a translation ratio (TR) between the height (H) measured in pixel space and a height (M) measured in machine space, wherein the height (M) is related to the distance (D)

wherein the distance (D) is measured in a number of steps (S) of a stepper motor;

the method further comprising: generating the translation ratio (TR) between the number of steps (S) and the height (H); and using the translation ratio (TR) to drive the nozzle tip to a predetermined drive depth (DD) in a sample container.

* * * * *